United States Patent [19]
Brimhall et al.

[11] Patent Number: 6,004,294
[45] Date of Patent: Dec. 21, 1999

[54] CATHETER AND INTRODUCER NEEDLE ASSEMBLY WITH NEEDLE SHIELD

[75] Inventors: Greg L. Brimhall, West Jordan; Stephen L. Thoresen, Orem; Weston F. Harding, Lehi; Glade H. Howell; Timothy J. Erskine, both of Sandy, all of Utah

[73] Assignee: Becton, Dickinson and Company, Franklin Lakes, N.J.

[21] Appl. No.: 09/057,718

[22] Filed: Apr. 9, 1998

[51] Int. Cl.⁶ .......................... A61M 5/178; A61M 5/00; A61M 5/32
[52] U.S. Cl. .......................... 604/164; 604/110; 604/198
[58] Field of Search .................. 604/110, 187, 604/162–165, 192, 195, 198, 263

[56] References Cited

U.S. PATENT DOCUMENTS

| | | | |
|---|---|---|---|
| Re. 34,416 | 10/1993 | Lemieux | 604/164 |
| 4,810,248 | 3/1989 | Masters et al. | 604/192 |
| 4,816,021 | 3/1989 | Sitar et al. | 604/192 |
| 4,832,696 | 5/1989 | Luther et al. | 604/164 |
| 4,846,811 | 7/1989 | Vanderhoof | 604/263 |
| 4,964,854 | 10/1990 | Luther | 604/166 |
| 5,085,648 | 2/1992 | Purdy et al. | 604/198 |
| 5,215,528 | 6/1993 | Purdy et al. | 604/164 |
| 5,409,461 | 4/1995 | Steinman | 604/110 |
| 5,558,651 | 9/1996 | Crawford et al. | 604/263 |
| 5,601,536 | 2/1997 | Crawford et al. | 604/263 |
| 5,613,952 | 3/1997 | Pressly, Sr. et al. | 604/110 |

*Primary Examiner*—Corrine McDermott
*Assistant Examiner*—Michael Hayes
*Attorney, Agent, or Firm*—Eric M. Lee

[57] ABSTRACT

A catheter and introducer needle assembly with needle shield is provided wherein the needle includes an enlarged diameter portion and a distally facing shoulder. The needle shield includes a means for engaging the distally facing shoulder to prevent unwanted distal movement of the needle once the needle has been withdrawn into the needle shield. The needle shield also includes a small diameter opening adjacent to its proximal portion to limit proximal movement of the needle out of the needle shield.

18 Claims, 12 Drawing Sheets

6,004,294

CATHETER AND INTRODUCER NEEDLE ASSEMBLY WITH NEEDLE SHIELD

BACKGROUND OF THE INVENTION

The subject invention relates to a catheter and introducer needle assembly that includes a needle shield that will safely shield the sharp distal tip of the introducer needle after the needle has been used to insert the catheter into a patient.

Catheters, particularly intravenous (IV) catheters, are used for infusing fluid, such as normal saline solution, various medicaments and total parenteral nutrition, into a patient or withdrawing blood from a patient. Peripheral IV catheters tend to be relatively short, and are on the order of about one and one-half inches in length. The most common type of IV catheter is an over the needle peripheral IV catheter. As its name implies, an over the needle catheter is mounted over an introducer needle having a sharp distal tip. The catheter and the introducer needle are assembled so that the distal tip of the introducer needle extends beyond the distal tip of the catheter with the bevel of the needle facing up away from the patient's skin.

The catheter and introducer needle assembly is inserted at a shallow angle through the patient's skin into a peripheral blood vessel, i.e a smaller blood vessel that is not connected directly to the heart but is one of the branches of the central blood vessels that is directly connected to the heart. In order to verify proper placement of the assembly in the blood vessel, the clinician confirms that there is flashback of blood in the needle and in a flashback chamber located at the proximal end of the needle which is typically formed as part of the needle hub. Once proper placement is confirmed, the clinician applies pressure to the blood vessel by pressing down on the patient's skin over the distal tip of the introducer needle and the catheter. This finger pressure occludes further blood flow through the introducer needle. The clinician withdraws the introducer needle, leaving the catheter in place, and attaches a fluid handling device to the catheter hub. Once the introducer needle is withdrawn from the catheter, it is a "blood contaminated sharp" and must be properly handled.

In recent years, there has been great concern over the contamination of clinicians with a patient's blood and a recognition that "blood contaminated sharps" must be immediately disposed. This concern has arisen because of the advent of currently incurable and fatal diseases, such as Acquired Immunosuppressive Deficiency Syndrome ("AIDS"), which can be transmitted by the exchange of body fluids from an infected person to another person. Thus, contact with the body fluid of an AIDS infected person must be avoided. As noted above, if an introducer needle has been used to place a catheter in the vein of an AIDS infected person, the introducer needle is a vehicle for the transmission of the disease. Although clinicians are aware of the need to properly handle "blood contaminated sharps", unfortunately in certain medical environments, such as emergency situations or as a result of inattention or neglect, needlesticks with contaminated introducer needles still occur.

As a result of the problem of accidental needlesticks by "blood contaminated sharps", various needle shields have been developed. Generally, such needle shields work for their intended purpose but could be improved. For example, some needle shields are bulky, difficult to use or require special features or techniques to be operative.

SUMMARY OF THE INVENTION

It is therefore an object of this invention to provide a needle shield that is compact.

It is another object of this invention to provide a needle shield that is simple and easy to use.

It is still another object of this invention to provide a needle shield that requires no special features or technique to be operative.

The catheter and introducer needle assembly with needle shield of this invention includes a catheter having a distal end and a proximal end connected to the distal end of a catheter hub. The introducer needle has a sharp distal tip and a proximal end connected to the distal end of a needle hub. A flashback chamber is defined in the needle hub. Typically a vented plug is located in the open proximal end of the flashback chamber to allow air to escape from the flashback chamber when blood enters the flashback chamber from the introducer needle. The catheter is coaxially disposed over the introducer needle so the sharp distal tip of the introducer needle is distal of the distal end of the catheter. The introducer needle also defines, along a distal portion thereof, an enlarged diameter portion with a distally facing shoulder immediately distal thereof and a tapered portion immediately proximal thereof. The enlarged diameter portion cooperates with a needle shield to prevent unwanted proximal movement of the introducer needle with respect to the needle shield once the introducer needle shield has been withdrawn into the needle shield after use. The distally facing shoulder cooperates with the needle shield to prevent unwanted distal movement of the introducer needle once the introducer needle has been withdrawn proximally into the needle shield after use.

The needle shield includes a main body portion defining a longitudinally extending passage through which the introducer needle extends. The needle shield also includes a means for engaging the distally facing shoulder of the enlarged diameter portion of the introducer needle to prevent distal movement of the introducer needle once the introducer needle has been proximally withdrawn into the needle shield. The longitudinally extending passage has a proximal portion, or a distal opening thereto, that has a diameter sufficient to allow the proximal portion of the introducer needle to extend therethrough but that is too small enough to allow the enlarged diameter portion of the introducer needle from passing therethrough.

The means for engaging the distally facing shoulder of the enlarged diameter portion of the introducer needle can take many forms. For example, a spring gate can be located in a hollow cavity portion of the main body portion of the needle shield and about a distal portion of the introducer needle distal. The spring gate has a generally U shaped configuration with a pair of tines. A biasing mechanism forces the spring gate up into contact with the introducer needle. When the introducer needle is withdrawn proximally into the needle shield, the spring gate rotates out of the way so the spring gate is generally parallel to the longitudinal axis of the introducer needle. In this manner, the enlarged diameter portion of the introducer needle rides past the tines. When the enlarged diameter portion passes by the tines so the distally facing shoulder is proximal of the spring gate, the biasing mechanism forces the spring gate into engagement with the shaft of the introducer needle. This ensures that the introducer needle engages the spring gate so the tines extend up past the introducer needle. If a clinician were to then try to advance the introducer needle distally, the distally facing shoulder would butt up against the spring gate which in turn would butt up against the distal wall of the cavity in the main body portion and prevent the introducer needle from being moved distally. Thus the sharp distal tip of the introducer needle would be prevented from being reexposed distally from the needle shield.

A variation of the spring gate discussed above is a leaf spring. The leaf spring has a proximal wall, a support leg and a locking leg. The support leg and the locking leg are configured into a generally V-shape, with the apex of the V facing distally. The locking leg is contoured to approximate a portion of the circumference of the introducer needle and rides along the introducer needle shaft. The configuration of the leaf spring ensures that the locking leg is biased toward the introducer needle but can be moved down away from the introducer needle so that it can ride over the enlarged diameter portion as the introducer needle is moved proximally into the needle shield. Once the distally facing shoulder is moved proximally of the proximal end of the locking leg of the leaf spring, the locking leg moves back into contact with the shaft of the introducer needle. If the introducer needle is moved distally, the proximal end of the locking leg of the leaf spring will engage the distally facing shoulder and prevent further distal movement of the introducer needle.

An alternative means for engaging the distally facing shoulder is a tube formed in the main body portion. The tube is coaxially located in the longitudinal passage of the main body portion and includes at least one movable lanced protrusion or tab that extends inwardly into the tube. Because the tab is movable, the distally facing shoulder can move proximally past the tab. Once the introducer needle has been withdrawn proximally into the needle shield such that the tab is distal of the distally facing shoulder, any distal movement of the introducer needle will be prevented when the distally facing shoulder engages the tab.

The distal portion of the needle shield includes a plurality of longitudinally extending fingers and radially inwardly extending projections that engage the proximal end of the catheter hub. This ensures that the needle shield remains engaged with the catheter until the introducer needle has been completely removed from the catheter and is safely shielded in the needle shield.

BRIEF DESCRIPTION OF THE DRAWINGS

The preferred embodiments are illustrated in the drawings in which like reference numerals refer to like elements and in which.

DETAILED DESCRIPTION OF THE INVENTION

Figure 1:
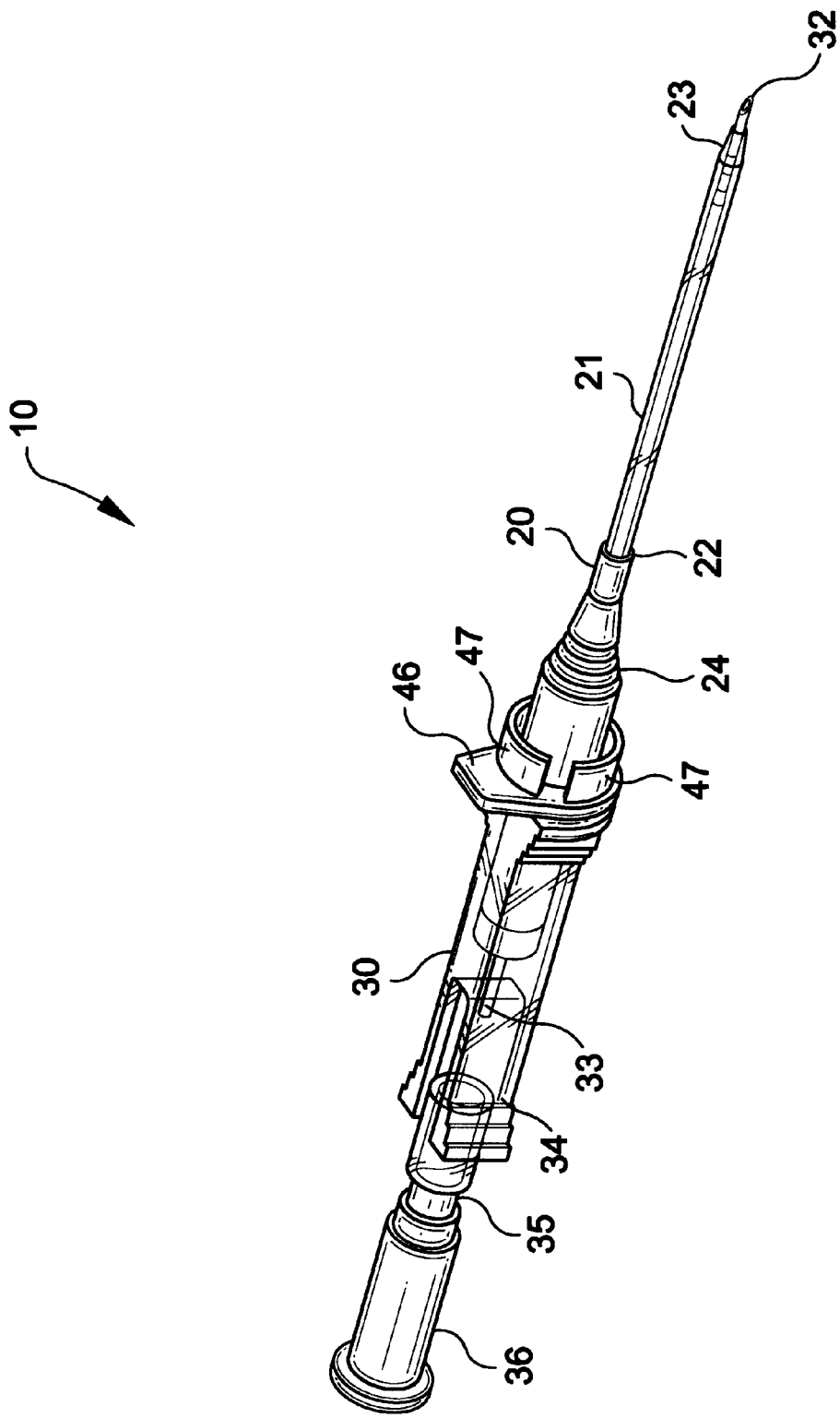
FIG. 1 is a perspective view of the catheter and introducer needle assembly with needle shield of this invention.

As used herein, the term "proximal" refers to a location on the catheter and introducer needle assembly with needle shield of this invention closest to the clinician using the device and farthest from the patient in connection with whom the device is used when the device is used in its normal operation. Conversely, the term "distal" refers to a location on the catheter and introducer needle assembly of this invention farthest from the clinician using the device and closest to the patient in connection with whom the device is used when the device is used in its normal operation.

The catheter and introducer needle assembly of this invention is identified generally by the numeral 10. It includes a catheter assembly 20 and an introducer needle assembly 30 that includes a needle shield 40.

Catheter assembly 20 includes a catheter 21 that has a proximal end 22, a distal end 23 and a catheter hub 24 affixed to catheter proximal end 22. Suitable materials for catheter 21 include, but are not limited to, thermoplastic resins such as polytetrafluoroethylene (PTFE), fluorinated ethylene propylene copolymer (FEP), polyurethane and the like. Preferably, catheter 21 is formed from a thermoplastic hydrophilic polyurethane that softens with exposure to physiological conditions present in the patient's body. Suitable materials for catheter hub 24 include, but are not limited to, thermoplastic polymeric resins such as polycarbonate, polystyrene, polypropylene and the like. Catheter hub 24 may include a radially outwardly extending tab, not shown, which is useful for advancing catheter 21 into the patient's blood vessel.

Introducer needle assembly 30 includes introducer needle 31 having a sharp distal tip 32 defined by bevel 32a and a proximal end 33 connected to needle hub 34. Introducer needle 31 is preferably formed from stainless steel. Needle hub 34 can include an integrated flashback chamber having an open proximal end 35. Needle hub 34 is preferably formed from the same types of materials that are used to form catheter hub 24. Preferably, open proximal end 35 is closed to fluid flow by a vented plug 36 which allows air but not fluid to flow therethrough.

Introducer needle assembly 30 also includes needle shield 40 which includes main body portion 41 and which in turn defines a longitudinally extending passage 42 having a proximal portion 43, a distal portion 44 and a distal opening 45. This allows introducer needle 31 to extend longitudinally through main body portion 41. The diameter of proximal portion 43 is slightly larger than the diameter of the main portion of introducer needle 31. This allows the main portion of introducer needle 31 to easily pass through proximal portion 43. Main body portion 41 also includes a radially extending flange 46 and a plurality of longitudinally extending fingers 47. Fingers 47 also include radially inwardly directed projections 48. Fingers 47 and projections 48 engage catheter hub 24 to hold introducer needle assembly 30 together with catheter assembly 20.

Figure 2:
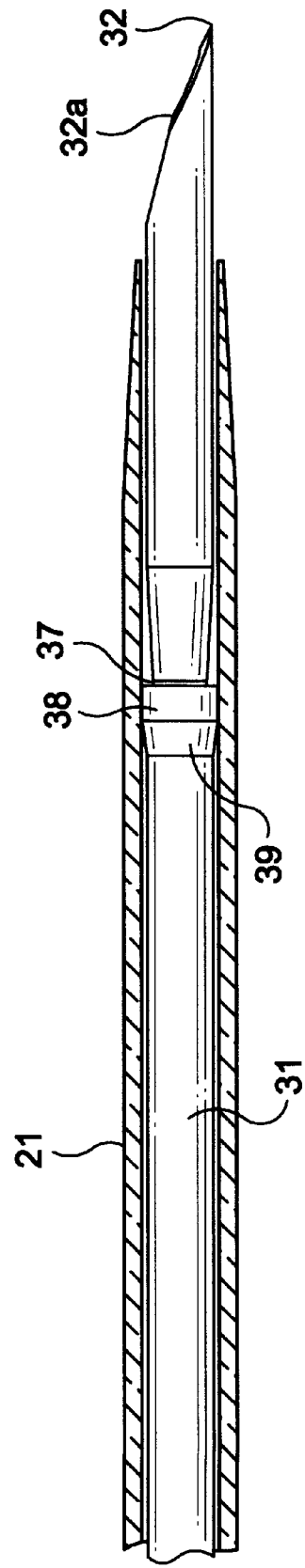
FIG. 2 is an enlarged elevation view, partially in cross-section, of the distal portion of the introducer needle used in the catheter and introducer needle assembly with needle shield of this invention.
Figure 3:
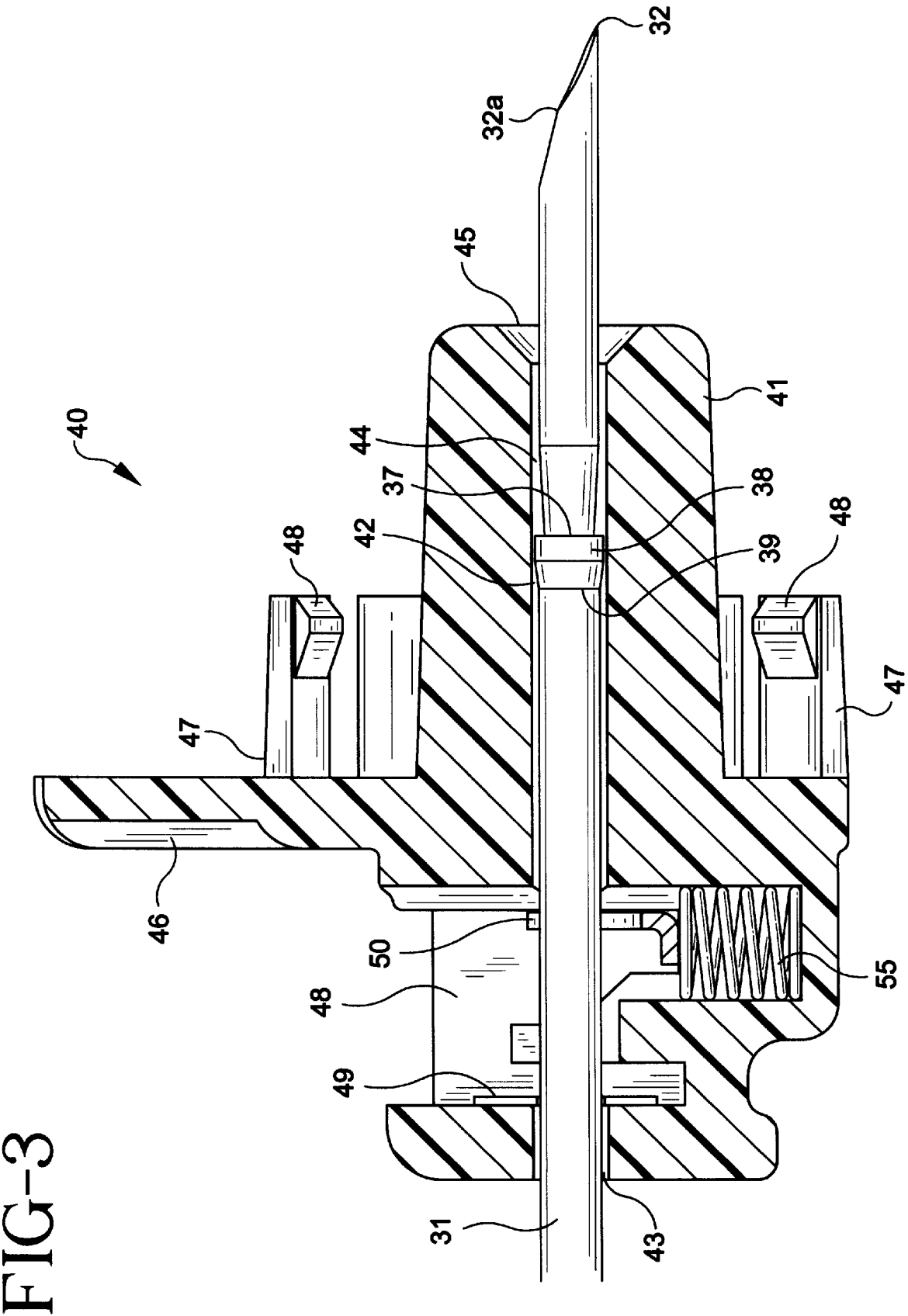
FIG. 3 is a cross-sectional view of one embodiment of the needle shield and the distal portion of the introducer needle where the sharp distal tip of the introducer needle is being withdrawn into the needle shield.
Figure 4:
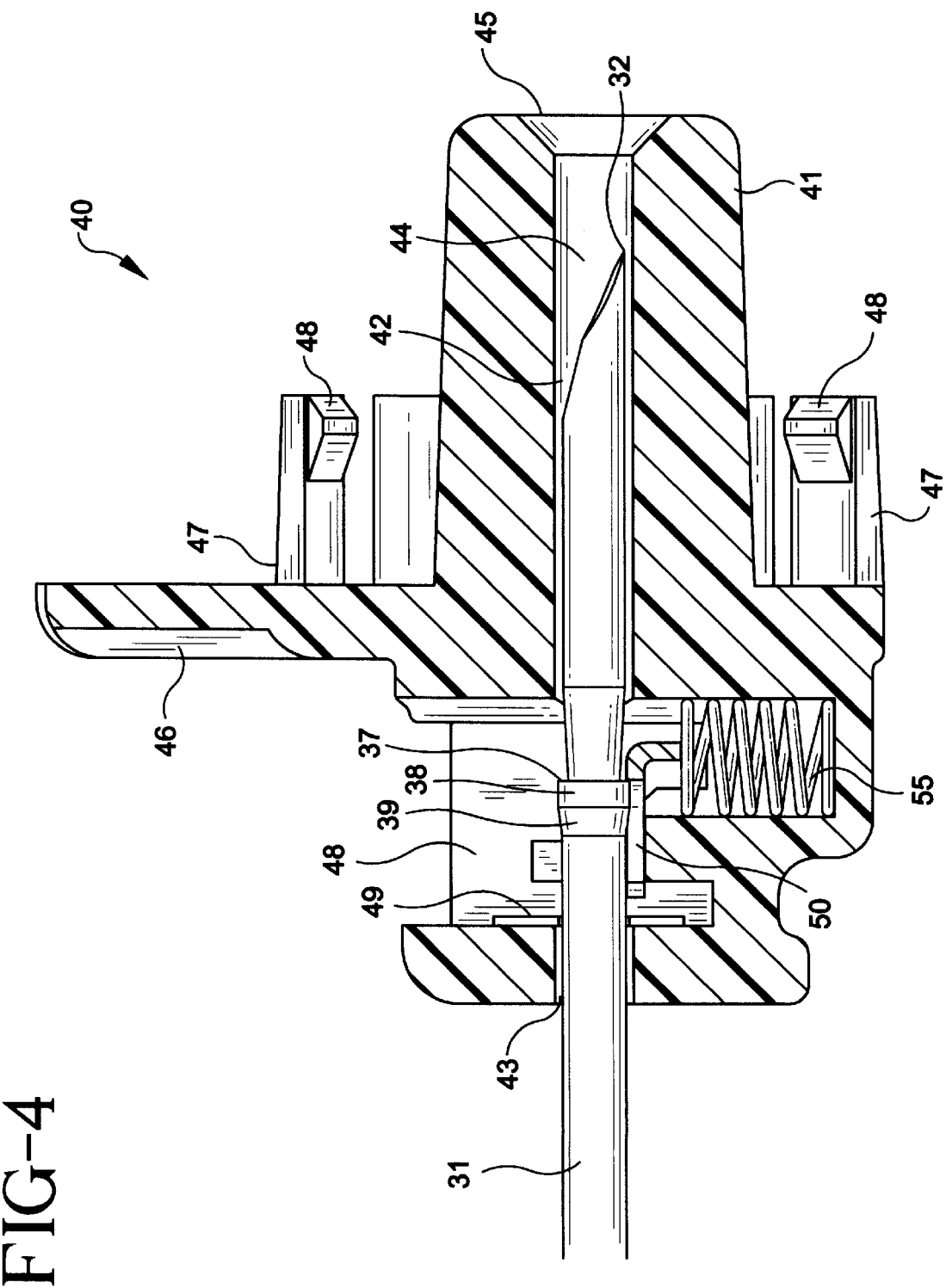
FIG. 4 is a cross-sectional view of the one embodiment of the needle shield and the distal portion of the introducer needle with the sharp distal tip of the introducer needle being withdrawn into the needle shield with the spring gate rotated out of the way.
Figure 5:
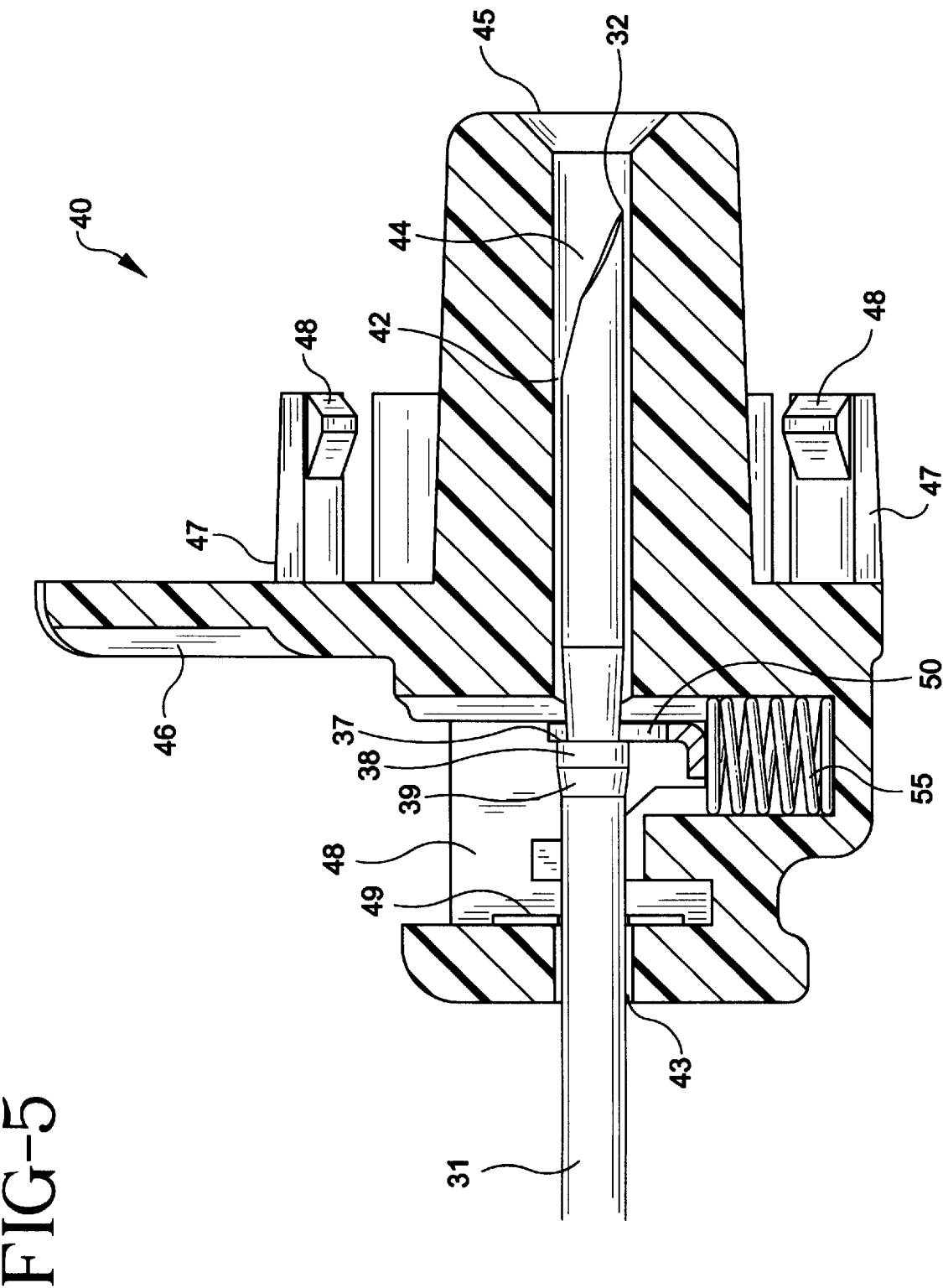
FIG. 5 is a cross-sectional view of the one embodiment of the needle shield and the distal portion of the introducer needle with the sharp distal tip of the introducer needle locked in the needle shield in its distal most position.
Figure 6:
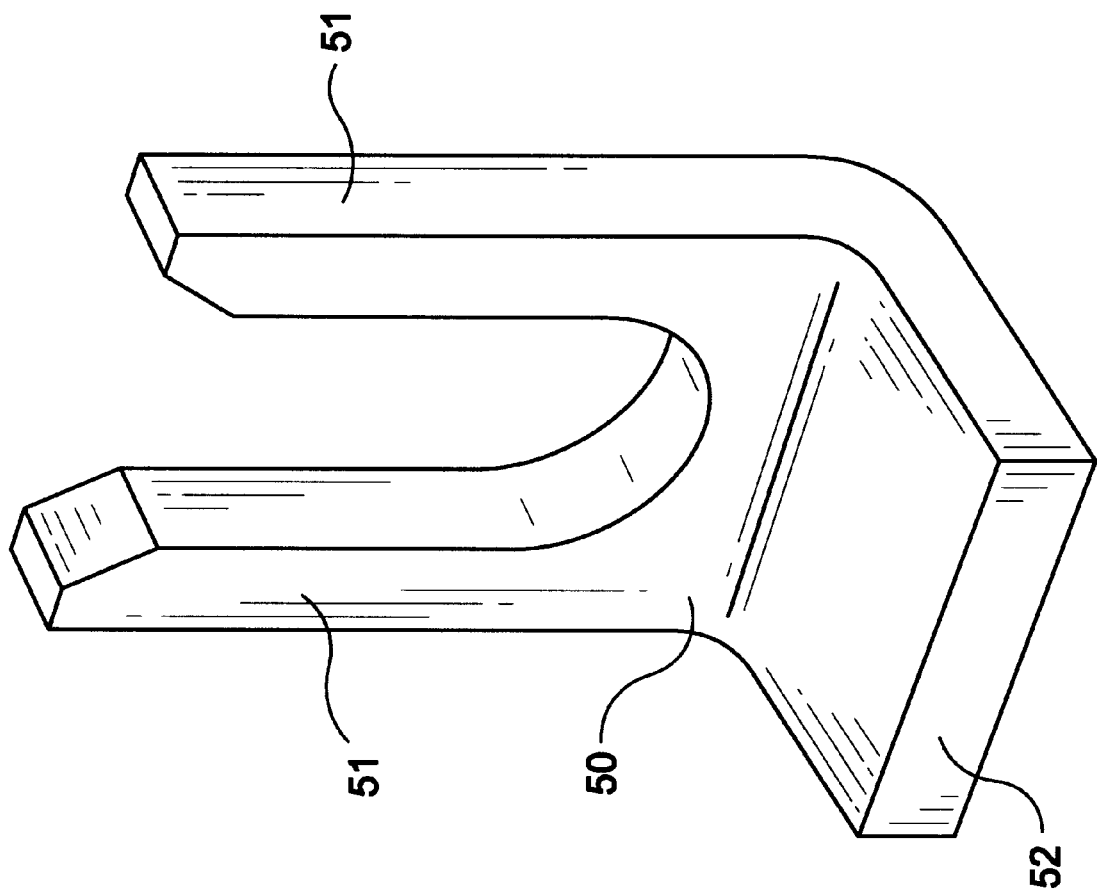
FIG. 6 is a perspective view of the spring gate that is used in the embodiment of FIGS. 3 through 5 to lock the introducer needle in the needle shield.

Introducer needle 31 includes a distally facing shoulder 37, an enlarged diameter portion 38 and a tapered proximal portion 39. See FIG. 2. Preferably, distally facing shoulder 37, enlarged diameter portion 38 and tapered proximal portion 39 are formed on introducer needle 31 by centerless grinding a larger diameter introducer needle. Enlarged diameter portion 38 should have a diameter greater than the diameter of proximal portion 43. This ensures that introducer needle 31 cannot be pulled in a proximal direction completely out of needle shield 40 because enlarged diameter portion 38 blocks further movement of introducer needle 31 through proximal portion 43. Alternatively, a washer 49 having an opening therein with a diameter smaller than the diameter of enlarged diameter portion 38 can be placed over the distal opening to proximal portion 43 of longitudinally extending passage 42 to prevent enlarged diameter portion 38 from passing into proximal portion 43.

The annulus formed by distally facing shoulder 37 against the shaft of introducer needle 31 should have a diameter of at least about 0.002 inches. It has been surprisingly found that this dimension is sufficient, when used in conjunction with needle shield 40 of this invention, to prevent introducer needle 31 from being moved distally out of needle shield 40 after introducer needle 31 has been withdrawn proximally into needle shield 40 to lock sharp distal tip 32 in needle shield 40. To ensure a sufficiently large diameter for the annulus of distally facing shoulder 37, that portion of introducer needle 31 immediately distal to distally facing shoulder 37 can be formed with a slightly increasing taper from distally facing shoulder 37 toward the distal end of introducer needle 31. This taper can be formed by grinding that portion of introducer needle 31 immediately distal of distally facing shoulder 37.

The means for engaging distally facing shoulder 37 of introducer needle 31 can take many forms. For example, as shown in FIGS. 3 through 6, a spring gate 50 can be used to lock introducer needle 31 in place in needle shield 40. Spring gate 50 is located in a hollow cavity portion 48 of main body portion 41 of needle shield 40 and about introducer needle 31. Spring gate 50 has a generally U shape with a pair of tines 51 that allow introducer needle 31 to pass through spring gate 50 between tines 51. The distance between times 51 is slightly larger than the diameter of that portion of introducer needle 31 that is immediately distal of enlarged diameter portion 38. A biasing mechanism 55 forces spring gate 50 up into contact with introducer needle 31 and ensures that spring gate 50 remains engaged with introducer needle 31. Biasing mechanism 55 may take any appropriate form. For example, it may be a helical spring as shown in the FIGS. or it may be a compressible rubber-like material that acts as a spring. Spring gate 50 also includes a seat 52 that extends generally perpendicular to tines 51 to ensure that spring gate 50 maintains contact with biasing mechanism 55 and remains in proper position.

When introducer needle 31 is withdrawn proximally into needle shield 40, introducer needle 31 rides past tines 51. As tapered proximal portion 39 passes by tines 51, spring gate 50 rotates its orientation so that it is generally parallel to the longitudinal axis of introducer needle 31. Biasing mechanism 55 facilitates this rotating motion. See FIG. 4. This allows enlarged diameter portion 38 to pass proximally past spring gate 50. Once enlarged diameter portion 38 is proximal of spring gate 50, biasing mechanism 55 forces spring gate back into engagement with introducer needle 31. When enlarged diameter portion 38 is proximal of spring gate 50, sharp distal tip 32 defined by bevel 32a is proximal of distal opening 45 and is thus safely located in needle shield 40. Distal movement of introducer needle 31 is prevented because distally facing shoulder 37 engages tines 51 which in turn engages the distal wall of cavity 48 to prevent distal movement of enlarged portion 38 into distal portion 44 of longitudinally extending passage 42. Thus, if a clinician were to then try to advance introducer needle 31 distally, biasing mechanism 55 would ensure that spring gate 50 is in contact with the distal portion of the shaft of introducer needle 31 and distally facing shoulder 37 would butt up against spring gate 50 which in turn would butt up against the distal wall. This would prevent introducer needle 31 from being moved distally and thus prevent sharp distal tip 32 of introducer needle 31 from being reexposed from needle shield 40. And as discussed above, further proximal movement of introducer needle 31 from needle shield 40 is prevented because enlarged diameter portion 38 blocks further proximal movement of introducer needle 31 through proximal portion 43.

Figure 7:
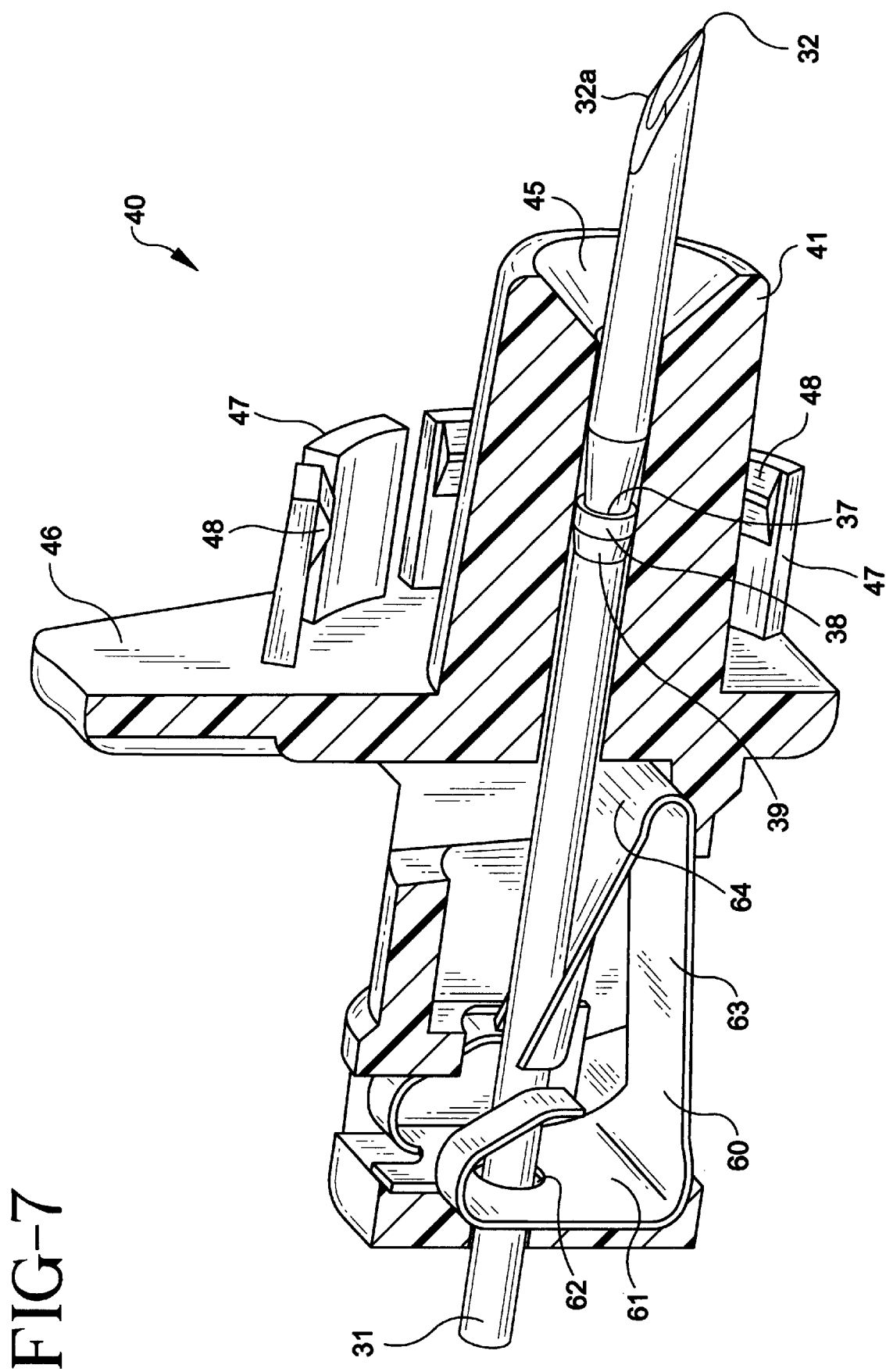
FIG. 7 is a perspective cross-sectional view of a second embodiment of the needle shield and the distal portion of the introducer needle with the sharp distal tip of the introducer needle extending from the distal end of the needle shield.
Figure 8:
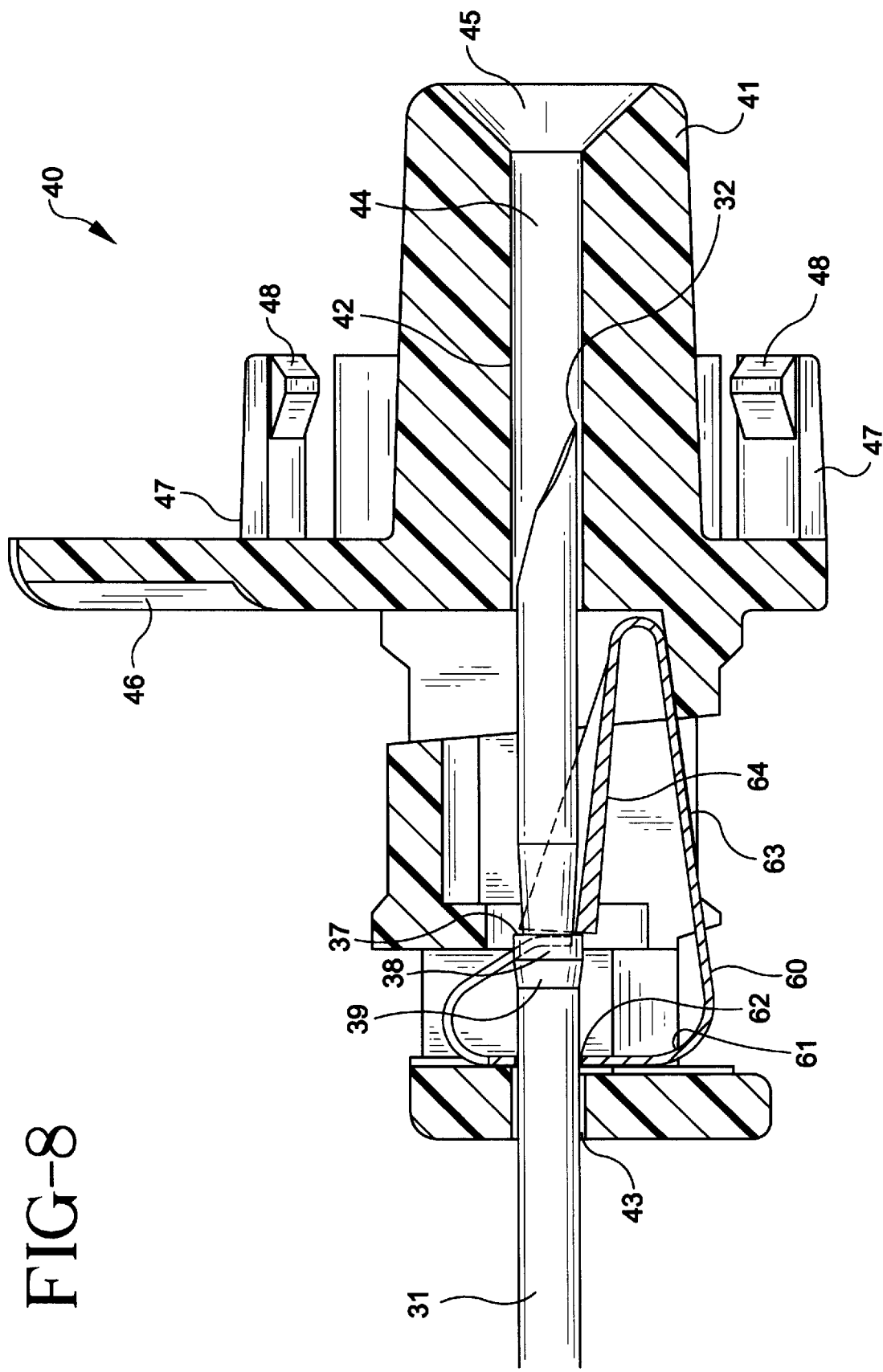
FIG. 8 is a cross-sectional view of the second embodiment of the needle shield and the distal portion of the introducer needle with the sharp distal tip of the introducer needle locked in the needle shield.
Figure 9:
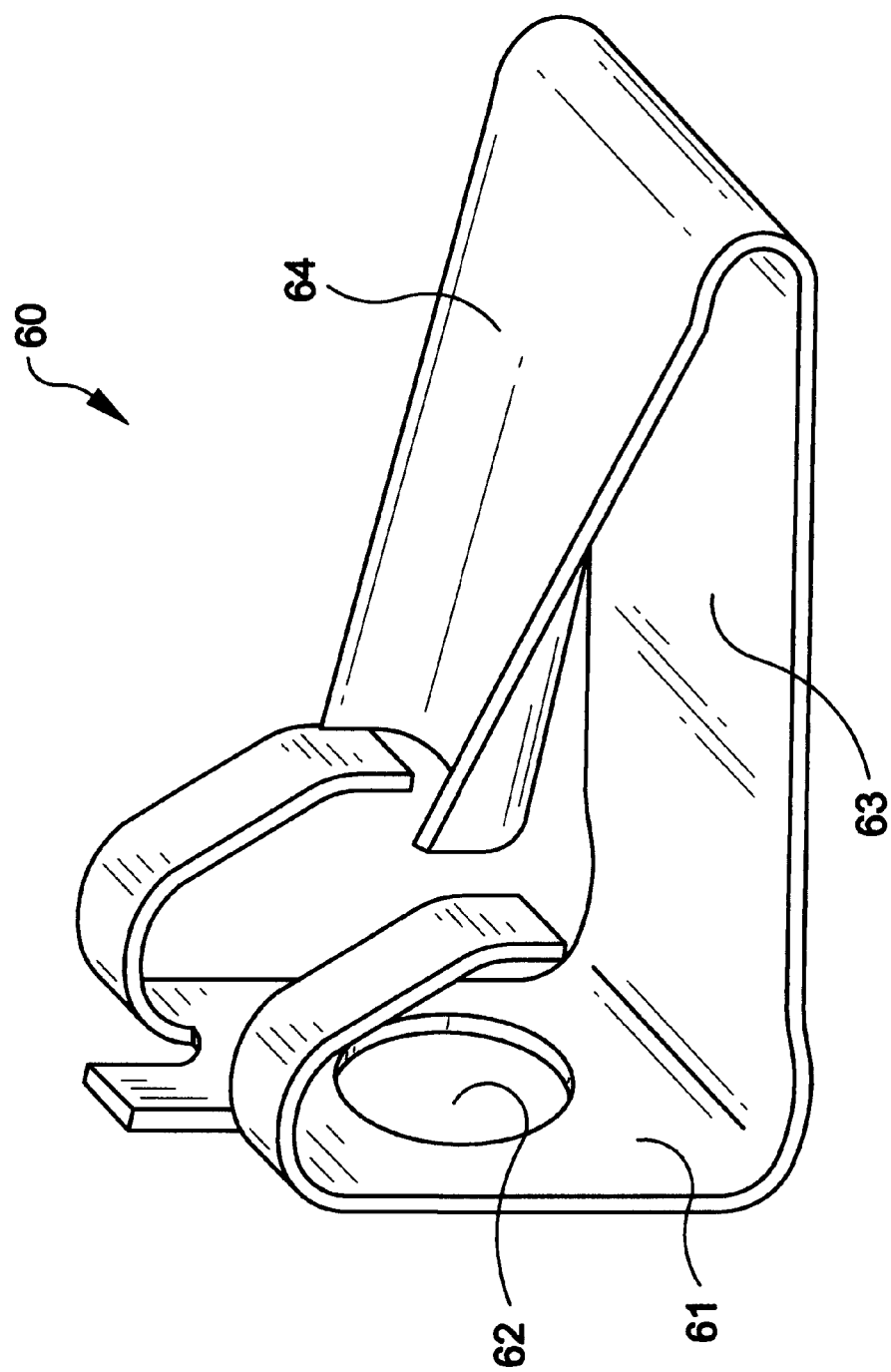
FIG. 9 is a perspective view of the leaf spring that is used in the embodiment of FIGS. 7 and 8 to lock the introducer needle in the needle shield.

A variation of spring gate 50 discussed above is to use a leaf spring 60. See FIGS. 7 through 9. Leaf spring 60 has a proximal wall 61 defining an opening 62 therein aligned with proximal portion 43 of longitudinally extending passage 42. Proximal wall 61 is generally perpendicular to the longitudinal axis of needle shield 40. Preferably the diameter of opening 62 is slightly larger than the diameter of the shaft of introducer needle 31 but smaller than the diameter of enlarged diameter portion 38. Leaf spring 60 also has a support leg 63 and a locking leg 64 which are configured into a generally V-shape, with the apex of the V facing distally. This V-shaped configuration ensures that locking leg 64 is biased toward introducer needle 31. Locking leg 64 is contoured along its proximal portion to form a generally semi-circular cross-section to approximate a portion of the circumference of introducer needle 31.

Locking leg 64 rides along the shaft of introducer needle 31 as introducer needle 31 is withdrawn proximally into needle shield 40. Locking leg 64 rides over tapered proximal portion 39 and enlarged diameter portion 38 as introducer needle 31 continues to be withdrawn into needle shield 40. Tapered proximal portion 39 facilitates movement of enlarged diameter portion 38 past locking leg 64. Once enlarged diameter portion 38 and distally facing shoulder 37 are moved proximally of the proximal end of locking leg 64, locking leg 64 moves back into contact with the shaft of introducer needle 31. If introducer needle 31 is moved distally, the proximal end of locking leg 64 will engage distally facing shoulder 37 and prevent further distal movement of introducer needle 31. Further proximal movement of introducer needle 31 is prevented by the engagement of enlarged diameter portion 38 with proximal wall 61.

Figure 10:
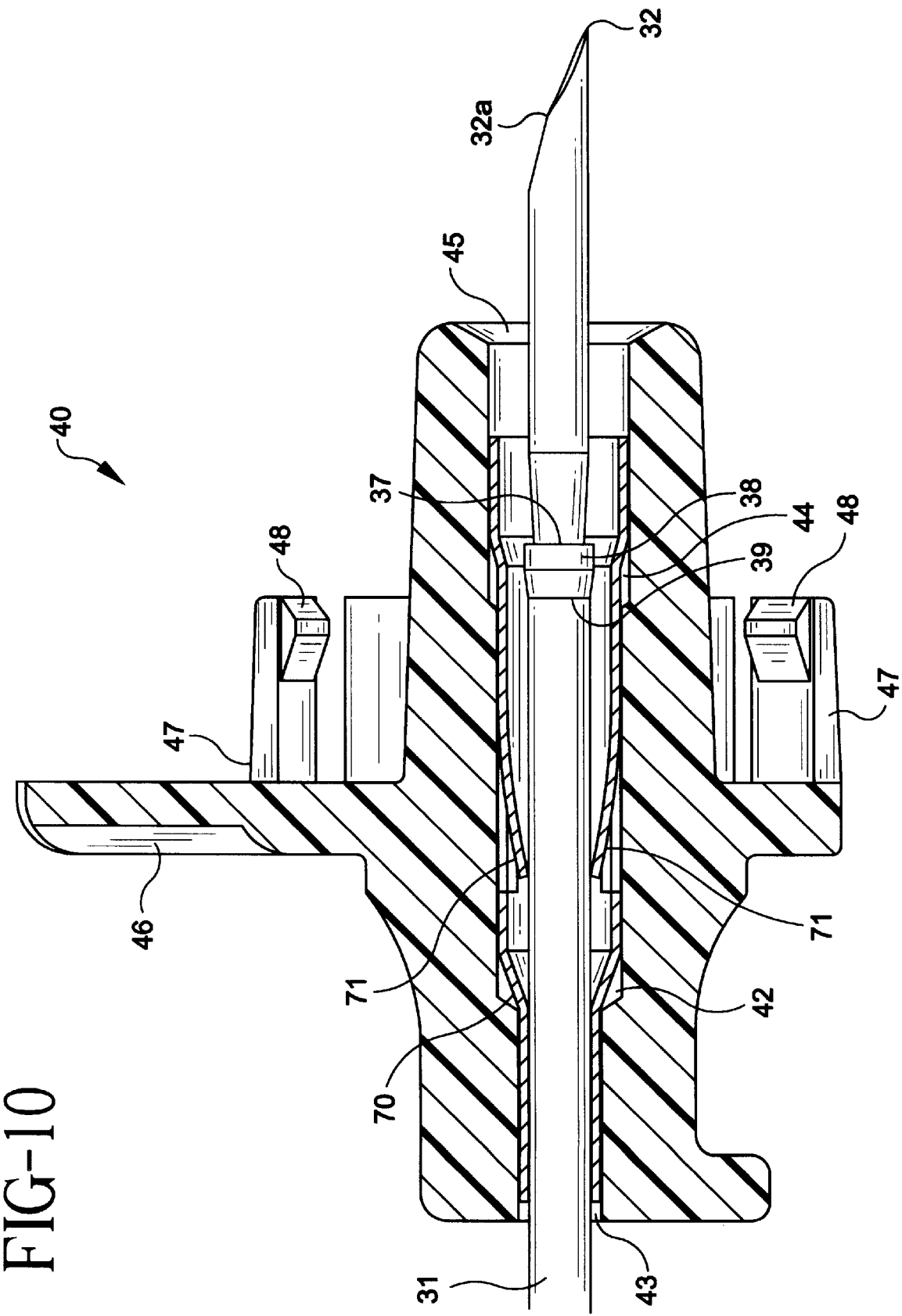
FIG. 10 is a cross-sectional view of a third embodiment of the needle shield and the distal portion of the introducer needle with the sharp distal tip of the introducer needle extending from the distal end of the needle shield.
Figure 11:
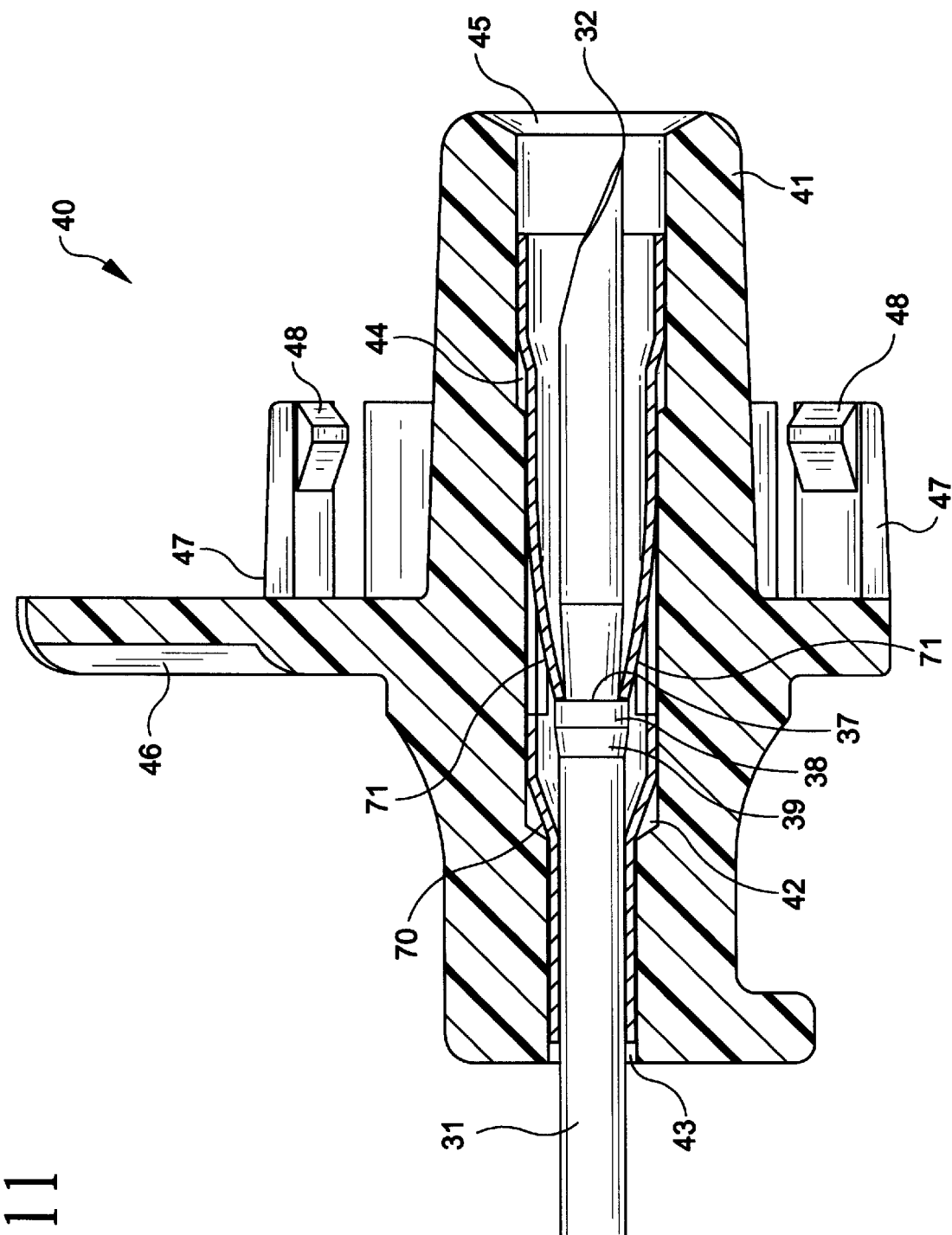
FIG. 11 is a cross-sectional view of the third embodiment of the needle shield and the distal portion of the introducer needle with the sharp distal tip of the introducer needle locked in the needle shield.
Figure 12:
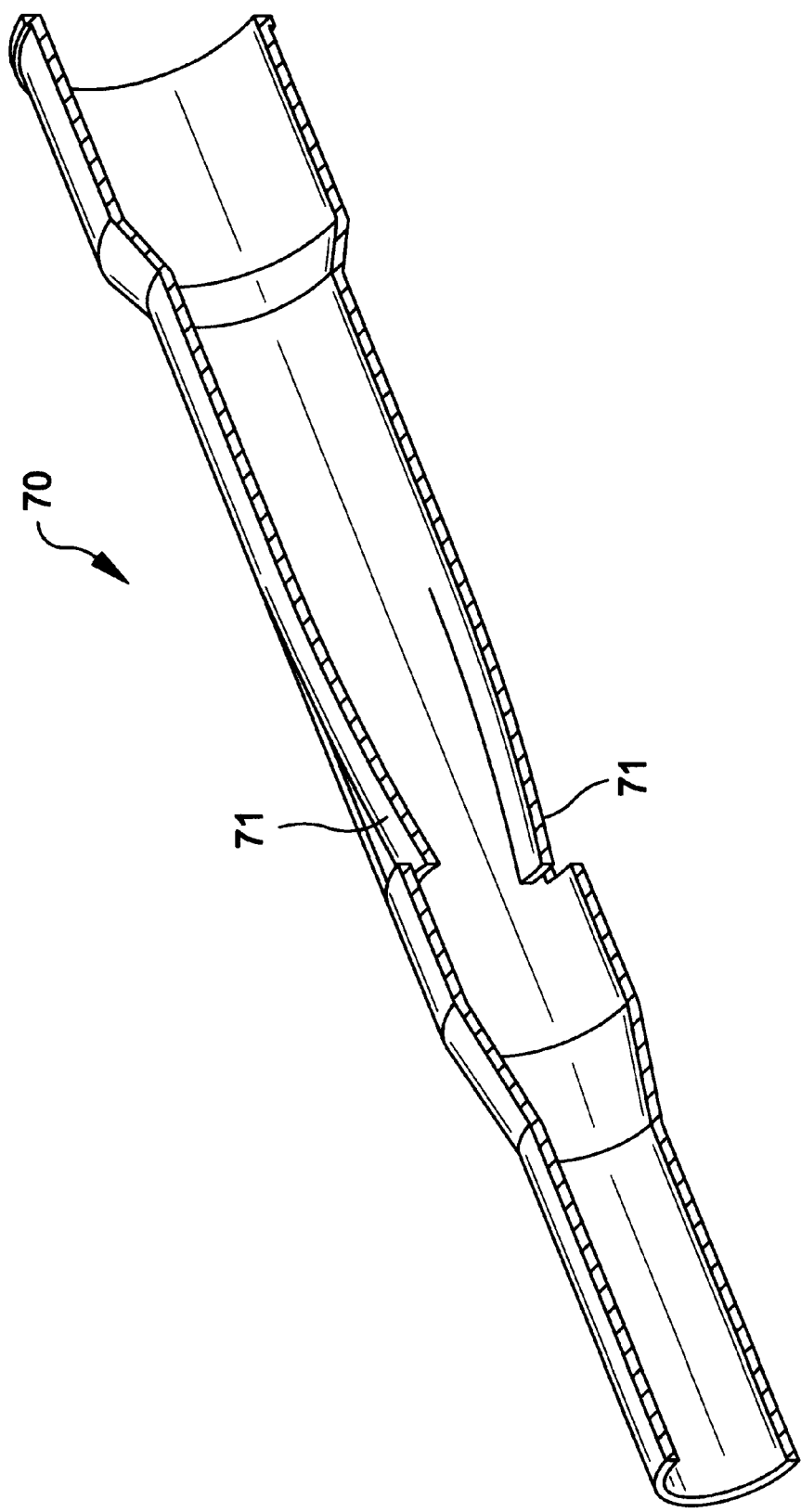
FIG. 12 is a perspective cross-sectional view of the tube that is used in the embodiment of FIGS. 10 and 11 to lock the introducer needle in the needle shield.

Another alternative means for engaging distally facing shoulder 37 is a tube 70 located in needle shield 40. See FIGS. 10 through 12. Tube 70 is coaxially located in longitudinally extending passage 42 and includes at least one movable lanced tab 71 that extends inwardly into tube 70. Preferably two such tabs 71 are formed on opposite sides of tube 70. Because tabs 71 are movable, tapered proximal portion 39 and enlarged diameter portion 38 can move past the proximal ends of tabs 71 as introducer needle 31 is withdrawn proximally into needle shield 40. Again the proximal movement of introducer needle 31 is facilitated by proximal tapered portion 39. Once introducer needle 31 has been withdrawn proximally into needle shield 40 such that tabs 71 are distal of distally facing shoulder 37, any distal movement of introducer needle 31 will be prevented by the engagement of the proximal ends of tabs 71 with distally facing shoulder 37. Further proximal movement of introducer needle 31 is prevented by the engagement of enlarged diameter portion 38 with proximal portion 43.

In order to place catheter 21 into a patient's blood vessel, the clinician substantially longitudinally aligns introducer needle 31 and catheter 21 with the target blood vessel. Bevel 32a should be facing substantially away from the skin surface during venipuncture. The clinician inserts introducer needle 31 and catheter 21 at a shallow angle, preferably less than about 35 degrees, into the skin so that sharp distal tip 32 enters the target blood vessel. The clinician then preferably observes a blood flashback in the flashback chamber of needle hub 34.

After confirming placement of introducer needle 31 and catheter 21 in the target blood vessel, the clinician advances catheter 21 distally axially along introducer needle 31 into position in the blood vessel. After proper placement of catheter 31 is achieved, the clinician places a finger from her other hand on the patient's skin over the blood vessel approximately over distal end of catheter 31. By placing her finger on the patient's skin and applying sufficient pressure on the skin, the clinican thereby substantially occludes blood flow through catheter 31. The clinican then withdraws introducer needle 31 from catheter 21 by moving needle hub 34 proximally. This movement causes introducer needle 31 to move proximally into needle shield 40. However, fingers 47 and projections 48 cause needle shield to remain engaged with catheter hub 22 during at least the initial proximal movement of introducer needle 31. Continued proximally directed force applied to needle hub 34 causes fingers 47 and projections 48 to become disengaged from catheter hub 21 once sharp distal tip 32 is located in needle shield 40 and introducer needle 31 is locked therein by one of the embodiments described above. After introducer needle 31 and needle shield 40 have been removed from catheter hub 21, the clinician may then attach any desired fluid handling device to catheter hub 21 and commence the planned treatment. Introducer needle 31 and needle shield 40 may then be disposed of according to the facility's disposal protocol.

Thus, it is seen that a catheter and introducer needle assembly with needle shield is provided that is compact, simple and easy to use and that requires no special features or technique to be operative.

We claim:

1. A catheter and introducer needle assembly, comprising:
   a catheter having a proximal end and distal end;
   a catheter hub in fluid communication with the catheter and having a proximal end and a distal end connected to the proximal end of the catheter;
   an introducer needle disposed in the catheter and having a proximal end and a distal end and defining an enlarged diameter portion having a proximal portion and wherein the introducer needle also defines a distally facing shoulder;
   a needle shield having a proximal end and a distal end removably connected to the catheter hub, the needle shield defining a longitudinally extending passageway therethrough with the introducer needle extending through the longitudinally extending passageway wherein the longitudinally extending passageway has a means adjacent to the proximal end for engaging the proximal portion of the enlarged diameter portion of the introducer needle to prevent unwanted proximal movement of the introducer needle and wherein the needle shield includes a separate means for engaging the distally facing shoulder to prevent unwanted distal movement of the introducer needle.

2. The catheter and introducer needle assembly of claim 1 wherein the means for engaging the enlarged diameter portion of the introducer needle to prevent unwanted proximal movement of the introducer needle is an opening into a proximal portion of the longitudinally extending passageway that has a diameter smaller than the diameter of the enlarged diameter portion of the introducer needle.

3. The catheter and introducer needle assembly of claim 2 wherein the means for engaging the distally facing shoulder to prevent unwanted distal movement of the introducer needle is a latch that is slidable along the introducer needle so as to be proximal of the enlarged diameter portion when the distal end of the introducer needle is distal of the distal end of the needle shield and distal of the enlarged diameter portion to allow the latch to engage the distally facing shoulder after the distal end of the introducer needle is withdrawn into the needle shield.

4. The catheter and introducer needle assembly of claim 3 wherein the latch has a generally U shaped gate and a biasing mechanism to bias the U shaped gate toward the introducer needle.

5. The catheter and introducer needle assembly of claim 3 wherein the latch is a tube defining at least one inwardly directed tab.

6. The catheter and introducer needle assembly of claim 3 wherein the latch is a leaf spring having one leg biased toward the introducer needle for engagement with the distally facing shoulder.

7. The catheter and introducer needle assembly of claim 6 wherein the leg is contoured along its proximal portion to approximate a portion of the circumference of the introducer needle.

8. A needle shield assembly, comprising:
   a needle having a proximal end and a distal end and defining an enlarged diameter portion having a proximal portion and wherein the needle also defines a distally facing shoulder; and
   a needle shield defining a longitudinally extending passageway therethrough with the needle extending through the longitudinally extending passageway wherein the longitudinally extending passageway has a proximal portion with a diameter less than the diameter of the enlarged diameter portion to prevent unwanted proximal movement of the needle with respect to the needle shield and wherein the needle shield includes a means spaced from the proximal portion of the longitudinally extending passageway for engaging the distally facing shoulder to prevent unwanted distal movement of the needle with respect to the needle shield.

9. The catheter and introducer needle assembly of claim 8 wherein the means for engaging the distally facing shoulder is a latch that is slidable along the needle so as to be proximal of the enlarged diameter portion when the distal end of the needle is distal of the distal end of the needle shield and distal of the enlarged diameter portion to allow the latch to engage the distally facing shoulder after the distal end of the needle is withdrawn into the needle shield.

10. The catheter and introducer needle assembly of claim 9 wherein the latch has a generally U shaped gate and a biasing mechanism to bias the U shaped gate toward the introducer needle.

11. The catheter and introducer needle assembly of claim 9 wherein the latch is a tube defining at least one inwardly directed tab.

12. The catheter and introducer needle assembly of claim 9 wherein the latch is a leaf spring having one leg biased toward the introducer needle for engagement with the distally facing shoulder.

13. The catheter and introducer needle assembly of claim 12 wherein the leg is contoured along its proximal portion to approximate a portion of the circumference of the introducer needle.

14. A needle shield assembly, comprising:

a needle having a proximal end and a distal end and defining an enlarged diameter portion thereon having a proximal portion and wherein the needle also defines a distally facing shoulder;

a needle shield defining a longitudinally extending passageway through which the needle extends and wherein the longitudinally extending passageway has a proximal portion with a diameter less than the diameter of the enlarged diameter portion to prevent unwanted proximal movement of the needle with respect to the needle shield, the needle shield having a proximal end and a distal end; and a latch spaced from the proximal portion of the longitudinally extending passageway operatively connected to the needle shield and slidable along the needle so as to be proximal of the enlarged diameter portion when the distal end of the needle is distal of the distal end of the needle shield and distal of the enlarged diameter portion to allow the latch to engage the distal facing shoulder after the distal end of the needle is withdrawn into the needle shield to prevent unwanted distal movement of the needle with respect to the needle shield.

15. The needle shield assembly of claim 14 wherein the latch has a generally U shaped gate and a biasing mechanism to bias the U shaped gate toward the introducer needle.

16. The needle shield assembly of claim 14 wherein the latch is a tube defining at least one inwardly directed tab.

17. The needle shield assembly of claim 14 wherein the latch is a leaf spring having one leg biased toward the introducer needle for engagement with the distally facing shoulder.

18. The catheter and introducer needle assembly of claim 17 wherein the leg is contoured along its proximal portion to approximate a portion of the circumference of the introducer needle.

* * * * *